United States Patent
Tomita et al.

(10) Patent No.: US 9,802,178 B2
(45) Date of Patent: Oct. 31, 2017

(54) CARRIER FOR BLOOD COMPONENT ADSORPTION AND BLOOD COMPONENT ADSORPTION COLUMN

(75) Inventors: Naotoshi Tomita, Otsu (JP); Yoshiyuki Ueno, Otsu (JP); Kazuhiro Tanahashi, Otsu (JP)

(73) Assignee: Toray Industries, Inc. (JP)

( * ) Notice: Subject to any disclaimer, the term of this patent is extended or adjusted under 35 U.S.C. 154(b) by 395 days.

(21) Appl. No.: 13/881,172

(22) PCT Filed: Oct. 26, 2011

(86) PCT No.: PCT/JP2011/074629
§ 371 (c)(1),
(2), (4) Date: Apr. 24, 2013

(87) PCT Pub. No.: WO2012/057185
PCT Pub. Date: May 3, 2012

(65) Prior Publication Data
US 2013/0220912 A1    Aug. 29, 2013

(30) Foreign Application Priority Data
Oct. 27, 2010    (JP) ................. 2010-241228

(51) Int. Cl.
| | | |
|---|---|---|
| *B01J 20/00* | (2006.01) | |
| *A61K 35/14* | (2015.01) | |
| *B01J 20/28* | (2006.01) | |
| *A61M 1/36* | (2006.01) | |
| *B01J 20/32* | (2006.01) | |

(52) U.S. Cl.
CPC ......... *B01J 20/28016* (2013.01); *A61K 35/14* (2013.01); *A61M 1/3679* (2013.01); *B01J 20/28004* (2013.01); *B01J 20/28023* (2013.01); *B01J 20/28038* (2013.01); *B01J 20/28054* (2013.01); *B01J 20/3251* (2013.01); *B01J 20/3285* (2013.01); *A61M 2202/0439* (2013.01); *Y10T 428/298* (2015.01); *Y10T 428/2982* (2015.01)

(58) Field of Classification Search
CPC ...... B01D 15/00; B01D 24/00; B01D 24/001; B01D 24/04; B01D 24/10; B01D 24/12; B01D 24/14; B01D 24/20; B01D 24/205; B01D 2101/00; B01D 39/02; B01D 39/04; B01D 39/06; B01D 39/16; B01D 2239/02; B01D 2239/025; B01D 2239/0258; B01D 2239/0471; B01D 2239/485; B01D 2239/0492; B01D 2239/1233

See application file for complete search history.

(56) References Cited

U.S. PATENT DOCUMENTS

| | | | |
|---|---|---|---|
| 4,701,267 A | | 10/1987 | Watanabe et al. |
| 6,037,458 A | * | 3/2000 | Hirai ............... B01D 15/00 530/380 |
| 2005/0214803 A1 | * | 9/2005 | Wang ............... C03C 17/30 435/6.12 |
| 2006/0264355 A1 | * | 11/2006 | Storr ............... A61L 2/0017 210/645 |
| 2009/0275874 A1 | | 11/2009 | Shimagaki et al. |

FOREIGN PATENT DOCUMENTS

| | | |
|---|---|---|
| CN | 101058058 | 10/2007 |
| JP | 60-087854 | 5/1985 |
| JP | 60-193468 A | 10/1985 |
| JP | 5-168707 A | 7/1993 |
| JP | 05-301043 | 11/1993 |
| JP | 6-007429 A | 1/1994 |
| JP | 7-080062 A | 3/1995 |
| JP | 2501500 B2 | 5/1996 |
| JP | 11-267421 A | 10/1999 |
| JP | 2001-310917 A | 11/2001 |
| JP | 2004-189724 A | 7/2004 |
| JP | 2006-312804 A | 11/2006 |
| JP | 2006-341087 A | 12/2006 |
| WO | 00/27496 | 5/2000 |
| WO | 2 058 018 | 5/2009 |

OTHER PUBLICATIONS

Dowex (2000), pp. 1-9.*
Supplementary European Search Report dated Apr. 2, 2014, of corresponding European Application No. 11836318.3.

* cited by examiner

Primary Examiner — Allison Fitzsimmons
(74) Attorney, Agent, or Firm — DLA Piper LLP (US)

(57) ABSTRACT

A carrier for blood component adsorption includes a water-insoluble carrier composed of a fiber or particle, the water-insoluble carrier having a surface to which a functional group(s) is/are introduced, the functional group(s) containing an acidic functional group selected from the group consisting of the sulfate group, sulfite group and sulfonate group; and containing an amino group; the fiber having a fiber diameter of, or the particle having a particle diameter of, 0.5 to 20 μm.

13 Claims, No Drawings

CARRIER FOR BLOOD COMPONENT ADSORPTION AND BLOOD COMPONENT ADSORPTION COLUMN

TECHNICAL FIELD

This disclosure relates to a carrier for blood component adsorption and a column for blood component adsorption.

BACKGROUND

Humoral factors such as inflammatory cytokines are deeply involved in causes of inflammatory diseases such as systemic lupus erythematosus, rheumatoid arthritis, multiple sclerosis, ulcerative colitis and Crohn's disease. Attempts are being made to treat inflammatory diseases by inactivating these humoral factors with biologicals such as low molecular drugs and antibodies. However, each of these humoral factors does not act alone on the site of inflammation. Plural humoral factors synergistically act to cause development and progression of inflammatory diseases. Thus, recent interest has focused on leukocytapheresis in which activated leukocytes per se as the source of humoral factors are removed.

Leukocytapheresis is a therapeutic method by blood purification wherein blood is collected from the vein and activated leukocytes are removed therefrom using, for example, a column filled with a carrier for adsorption, followed by returning the purified blood into the vein in the opposite side. Leukocytes can be roughly divided into 3 types, that is, granulocytes, monocytes and lymphocytes. Since leukocytes directly involved in inflammation caused by inflammatory diseases are considered to be granulocytes and monocytes, a carrier that selectively adsorbs granulocytes (JP 2501500 B2) and a carrier that selectively adsorbs both activated granulocytes and monocytes as well as inflammatory cytokines (JP 2006-312804 A and JP 7-080062 A) have been developed.

On the other hand, lymphocytes are also known to be indirectly involved in inflammation caused by inflammatory diseases. There is also a view that not only granulocytes and monocytes, but also lymphocytes should be removed by adsorption to achieve rapid healing of a severe inflammatory disease in a patient. Therefore, a carrier that can adsorb all of the 3 types of leukocytes, that is, granulocytes, monocytes and lymphocytes, has also been developed (JP 60-193468 A and JP 2001-310917 A).

However, the carrier that allows adsorption of all of the 3 types of leukocytes, that is, granulocytes, monocytes and lymphocytes, is composed of a non-woven fabric prepared from an ultrafine fiber, which non-woven fabric has a high bulk density. Since most blood components other than erythrocytes are filtered out and pressure loss occurs during blood circulation, safety problems such as stopping of the circulation and leakage of blood have been pointed out. On the other hand, although a powerful leukocyte-removing carrier that can adsorb not only all of the 3 types of leukocytes, but also inflammatory cytokines has been demanded, no successful development of such a carrier has been reported so far because of difficulty in overcoming the above problem.

It could therefore be helpful to provide a carrier for blood component adsorption which can remove leukocytes including all of granulocytes, monocytes and lymphocytes by adsorption while suppressing occurrence of pressure loss during blood circulation, which carrier can also remove inflammatory cytokines by adsorption at the same time.

SUMMARY

We discovered a carrier for blood component adsorption that causes less pressure loss due to clogging and can remove granulocytes, monocytes and lymphocytes as well as inflammatory cytokines with high efficiency by adsorption.

We thus provide a carrier for blood component adsorption and a column for blood component adsorption as follows:

(1) A carrier for blood component adsorption comprising a water-insoluble carrier composed of a fiber or particle, the water-insoluble carrier having a surface to which a functional group(s) is/are introduced, the functional group(s) containing an acidic functional group selected from the group consisting of the sulfate group, sulfite group and sulfonate group; and containing an amino group; the fiber having a fiber diameter of, or the particle having a particle diameter of, 0.5 to 20 μm.

(2) The carrier for blood component adsorption according to (1), wherein the water-insoluble carrier has a porosity of 85 to 98%.

(3) The carrier for blood component adsorption according to (1) or (2), wherein the water-insoluble carrier has an amount of negative charge of $1.5 \times 10^{-5}$ to $1.5 \times 10^{-3}$ eq/g.

(4) The carrier for blood component adsorption according to any one of (1) to (3), wherein the water-insoluble carrier is a fiber having a fiber diameter of 4 to 10 μm.

(5) The carrier for blood component adsorption according to any one of (1) to (4), wherein the acidic functional group and the amino group are linked together via an alkyl chain.

(6) The carrier for blood component adsorption according to (5), wherein the alkyl chain is an alkyl chain having not more than 3 carbon atoms.

(7) A column for blood component adsorption filled with the carrier for blood component adsorption according to any one of claims (1) to (6).

With our carrier for blood component adsorption, all of the 3 types of leukocytes, that is, granulocytes, monocytes and lymphocytes, can be efficiently removed by adsorption from blood of a patient with an inflammatory disease and inflammatory cytokines can also be removed by adsorption at the same time. Further, a column for blood component adsorption filled with the carrier for blood component adsorption can be used for leukocytapheresis, and may be suitably used in treatment of a severe inflammatory disease.

DETAILED DESCRIPTION

The carrier for blood component adsorption comprises a water-insoluble carrier composed of a fiber or particle, which water-insoluble carrier has a surface to which a functional group(s) is/are introduced, which functional group(s) contain(s) an acidic functional group selected from the group consisting of the sulfate group, sulfite group and sulfonate group; and contain(s) an amino group, which fiber has a fiber diameter of, or which particle has a particle diameter of, 0.5 to 20 μm.

The "carrier for blood component adsorption" means a material with which a blood component(s) can be removed from blood by adsorption.

The blood component means a component constituting blood. Examples of the blood component include blood cell components such as erythrocytes, leukocytes and platelets and humoral factors such as inflammatory cytokines. For the purpose of treatment of an inflammatory disease, leukocytes and inflammatory cytokines are preferably removed by adsorption.

The inflammatory cytokine means a protein secreted from a cell and transmits information to a specific cell. Examples of the inflammatory cytokine include interleukins, tumor necrosis factor-α, transforming growth factor beta, interferon-γ (hereinafter referred to as INF-γ), angiogenic growth factors and immunosuppressive acidic protein.

The interleukin means a cytokine secreted from a leukocyte and functions to control the immune system. Examples of the interleukin include interleukin-1, interleukin-6, interleukin-8 (hereinafter referred to as IL-8), interleukin-10 and interleukin-17 (hereinafter referred to as IL-17).

The adsorption means a state where a blood component is adsorbed to the carrier for blood component adsorption and not easily detached.

Examples of the material of the "water-insoluble carrier composed of a fiber or particle" include polyolefins such as polyethylene and polypropylene; polyesters such as polyethylene terephthalate and polybutylene terephthalate; fluorinated polymers such as Teflon (registered trademark); polysulfone-based polymers such as poly(p-phenylene ether sulfone); polyetherimides; polyimides; polyamides; polyethers; polyphenylene sulfides; polystyrenes; and acrylic polymers; and materials prepared by blending or alloying of these macromolecular compounds. For easy introduction of a functional group to the surface of the water-insoluble carrier, polystyrenes are preferred and, in view of heat resistance or retention of the shape upon processing, polypropylene or polypropylene-polyethylene copolymers are preferred.

The "functional group containing an acidic functional group selected from the group consisting of the sulfate group, sulfite group and sulfonate group; and containing an amino group" means a functional group containing in a part of the chemical structure of the functional group at least one each of: an acidic functional group selected from the group consisting of the sulfate group, sulfite group and sulfonate group; and an amino group.

The sulfate group (—OSO$_2$OH), sulfite group (—O(SO)OH) and sulfonate group (—SO$_2$OH) have chemical structures similar to each other, and each of these groups has an acidic hydroxyl group. Therefore, these groups show common characteristics such as strong acidity and negativity.

The acidic functional group is preferably positioned at a terminus of the above-described functional group in view of achieving easy interactions between the acidic functional group and blood components.

The amino group is preferably a secondary amino group, more preferably a tertiary amino group.

In the chemical structure of the above-described functional group, the chemical structure existing between the acidic functional group and the amino group, that is, the chemical structure linking the acidic functional group to the amino group (hereinafter referred to as the spacer), is preferably constituted of a hydrogen atom(s), carbon atom(s), oxygen atom(s), nitrogen atom(s), sulfur atom(s) and/or silicon atom(s). The spacer is more preferably an alkyl chain, still more preferably an alkyl chain having not more than 3 carbon atoms. In cases where the spacer is too large, the density of the acidic functional group decreases so that the number of atoms constituting the spacer is preferably not more than 200.

Examples of the reactive functional group that mediates linking between the water-insoluble carrier and the above-described functional group when the "functional group containing an acidic functional group selected from the group consisting of the sulfate group, sulfite group and sulfonate group; and containing an amino group" is to be introduced to the surface of the water-insoluble carrier include active halogen groups such as the halomethyl group, haloacetyl group, haloacetamidomethyl group and halogenated alkyl group; epoxide group; carboxyl group; isocyanate group; thioisocyanate group; and acid anhydride group. To have an appropriate degree of reactivity, active halogen groups are preferred, and the haloacetamidomethyl group is more preferred.

The above-described functional group wherein an acidic functional group is positioned as a terminus and the spacer is an alkyl chain can be obtained by, for example, reacting a commercially easily available aminoalkylsulfonic acid with a haloacetamidomethyl group. In particular, the above-described functional group wherein the spacer is an alkyl chain having not more than 3 carbon atoms can be obtained by reacting aminoethylsulfonic acid (hereinafter referred to as taurine) or 3-aminopropiosulfonic acid (hereinafter referred to as homotaurine), or N-methylaminoethylsulfonic acid (hereinafter referred to as N-methyltaurine) or 1,3-propanesultone (hereinafter referred to as propanesultone) with a haloacetamidomethyl group.

The "fiber diameter of the fiber" and "particle diameter of the particle" of the "water-insoluble carrier composed of a fiber or particle" needs to be "0.5 to 20 μm" for exertion of the phagocytic activity of leukocytes, and the fiber diameter and the particle diameter are preferably 4 to 20 μm, more preferably 4 to 10 μm in view of more stable exertion of the phagocytic activity. The lower limit of the fiber diameter and the particle diameter is preferably 0.5 μm, more preferably 4 μm. The upper limit of the fiber diameter and the particle diameter is preferably 20 μm, more preferably 10 μm. Either preferred lower limit may be combined with either preferred upper limit. The phagocytic activity of leukocytes herein means the property of granulocytes and monocytes to capture and eat microorganisms and bacteria which have invaded into the body of human or the like.

The "fiber diameter of a fiber" means the mean of values obtained by randomly collecting 10 samples of small pieces of the fiber and taking a photograph of each sample using a scanning electron microscope at a magnification of 2,000×, followed by measuring the diameter of the fiber at 10 locations per photograph (100 locations in total). Similarly, the "particle diameter of a particle" means the mean of values obtained by randomly collecting 10 samples of small pieces of the particle and taking a photograph of each sample using a scanning electron microscope at a magnification of 2,000×, followed by measuring the diameter of the particle at 10 locations per photograph (100 locations in total).

In cases where the fiber diameter of the fiber is less than 10 μm, a fiber having a larger diameter may be mixed in view of securing strength of the carrier for blood component adsorption, and the fiber diameter of such a fiber having a larger diameter is preferably 10 to 50 μm.

Examples of the shape of the water-insoluble carrier composed of a fiber include a woven fabric, non-woven fabric, cotton cloth and hollow fiber. In cases where the shape is a non-woven fabric, a scaffold fiber such as polypropylene is also preferably included for maintaining the shape.

Removal of blood components using the carrier for blood component adsorption is not based on the principle of filtration, but is based on utilization of the phagocytic ability of granulocytes and monocytes and on utilization of interactions of lymphocytes and inflammatory cytokines with the "functional group containing an acidic functional group selected from the group consisting of the sulfate group, sulfite group and sulfonate group; and containing an amino group", to remove the respective blood components by adsorption. Accordingly, in cases where the carrier for blood component adsorption is used by filling a container such as a column with the carrier, the porosity can be increased and the pressure loss can be largely reduced compared to cases where a conventional technique is used. On the other hand, since, in cases where the porosity is too large, the shape of the adsorptive carrier can be hardly maintained, the porosity of the water-insoluble carrier is preferably 85 to 98%, more preferably 90 to 95%. The lower limit of the porosity is preferably 85%, more preferably 90%. The upper limit of the porosity is preferably 98%, more preferably 95%. Either preferred lower limit may be combined with either preferred upper limit.

The "porosity" is the ratio of the volume of the void in the carrier for blood component adsorption, and means the percentage value calculated by dividing the volume of the void in the carrier for blood component adsorption by the apparent volume of the carrier for blood component adsorption. More specifically, a cross-sectional photograph of the carrier for blood component adsorption was taken using a scanning electron microscope at a magnification of 200× and, based on the result of image analysis of the photograph, the porosity was calculated according to Equation 1:

$$\text{Porosity (\%)} = \{(b-a)/b\} \times 100 \quad \text{Equation 1}$$

a: The area of the part occupied by the water-insoluble carrier b: The total area of the cross-section of the carrier for blood component adsorption.

The acidic functional group contained in the "functional group containing an acidic functional group selected from the group consisting of the sulfate group, sulfite group and sulfonate group; and containing an amino group" is assumed to largely contribute to adsorption of lymphocytes. On the other hand, in cases where the density of the acidic functional group is too large, competitive adsorption is assumed to occur between lymphocytes and proteins with positive charges, leading to a reduced adsorption rate of lymphocytes. The density of the acidic functional group can be represented as the amount of negative charge. The amount of negative charge of the carrier for blood component adsorption is preferably $1.5 \times 10^{-5}$ to $1.5 \times 10^{-3}$ eq/g, more preferably $1.0 \times 10^{-4}$ to $1.0 \times 10^{-3}$ eq/g. The lower limit of the amount of negative charge is preferably $1.5 \times 10^{-5}$ eq/g, more preferably $1.0 \times 10^{-4}$ eq/g. The upper limit of the amount of negative charge is preferably $1.5 \times 10^{-3}$ eq/g, more preferably $1.0 \times 10^{-3}$ eq/g. Either preferred lower limit may be combined with either preferred upper limit. An amount of negative charge of 1 eq/g herein means that 1 g of the adsorptive carrier can adsorb 1 mol of protons.

The acidic functional group contained in the "functional group containing an acidic functional group selected from the group consisting of the sulfate group, sulfite group and sulfonate group; and containing an amino group" is also assumed to contribute to adsorption of inflammatory cytokines to some extent. That is, since inflammatory cytokines are proteins of about 1 to several 10 kDa comprising many kinds of ionic amino acids, it is assumed that portions having positive charges in the protein molecules interact with the negative acidic functional group.

The container shape of the column for blood component adsorption filled with the carrier for blood component adsorption is not restricted as long as the container has an inlet and an outlet for blood. Examples of the container include prism-shaped containers such as cylindrical, triangular prism-shaped, quadrangular prism-shaped, hexagonal prism-shaped and octagonal prism-shaped containers. The container is preferably a container which can be filled with the carrier for blood component adsorption in a laminated form, a container which can be filled with the carrier for blood component adsorption wound into a cylindrical shape, or a container wherein blood flows from the circumference of a cylinder into the inside thereof, followed by flowing to the outside of the container.

EXAMPLES

The column for blood component adsorption will now be described in more detail by way of experimental examples. In Examples, wt % represents % by weight.

Preparation of Non-Woven Fabric Made of PP

A sea-island composite fiber having 36 islands each of which further has a core/sheath complex was obtained using the following components under the conditions of a spinning rate of 800 m/minute and a draw ratio of 3.

The core component of the island: polypropylene.

The sheath component of the island: 90 wt % polystyrene and 10 wt % polypropylene.

The sea component: copolymerized polyester comprising ethylene terephthalate units as major repeating units and 3 wt % 5-sodium sulfoisophthalic acid as a copolymerization component.

The composite ratio (weight ratio): core:sheath:sea=45:40:15.

After preparing a non-woven fabric composed of this fiber in an amount of 85 wt % and a polypropylene fiber having a diameter of 20 µm in an amount of 15 wt %, a sheet-shaped polypropylene net (thickness, 0.5 mm; single fiber diameter, 0.3 mm; aperture, 2 mm×2 mm) was sandwiched between two sheets of this non-woven fabric, and the resultant was needle-punched to obtain a non-woven fabric having a three-layer structure (hereinafter referred to as the non-woven fabric made of PP).

Preparation of Non-Woven Fabric Made of PSt+PP

The non-woven fabric made of PP was treated at 95° C. with 3 wt % aqueous sodium hydroxide solution to dissolve the sea component. By this, a non-woven fabric having a diameter of the core/sheath fiber of 5 µm and a bulk density of 0.02 g/cm³ (non-woven fabric made of PSt+PP, hereinafter referred to as the non-woven fabric A) was prepared.

Preparation of Chloroacetamidomethyl-Modified Non-Woven Fabric

At not more than 10° C., 46 wt % nitrobenzene, 46 wt % sulfuric acid, 1 wt % paraformaldehyde and 7 wt % N-methylol-α-chloracetamide (hereinafter referred to as NMCA) were mixed together, and the resulting mixture was stirred and dissolved to prepare a reaction liquid for NMCA modification. The temperature of this reaction liquid for NMCA modification was adjusted to 5° C., and the reaction liquid for NMCA modification was added to the non-woven fabric A at a solid/liquid ratio corresponding to about 40 mL of the reaction liquid for NMCA modification with respect to 1 g of the non-woven fabric A. The reaction mixture was left to stand at 5° C. in a water bath to allow the reaction to proceed for 2 hours. Thereafter, the non-woven fabric was removed from the reaction mixture, and immersed in nitrobenzene in the same amount as the reaction liquid for NMCA treatment for washing. Subsequently, the non-woven fabric was removed therefrom, and immersed in methanol for washing to obtain a chloroacetamidomethyl-modified non-woven fabric (hereinafter referred to as the non-woven fabric B).

Preparation of Tetraethylenepentamine-Modified Non-Woven Fabric

Tetraethylenepentamine (hereinafter referred to as TEPA) and triethylamine were dissolved in 500 mL of dimethyl sulfoxide (hereinafter referred to as DMSO) such that their concentrations are 20 mM and 473 mM, respectively. In the resulting solution, 10 g of the non-woven fabric B was immersed, and the reaction was allowed to proceed at 40° C. for 3 hours. The non-woven fabric after the reaction was washed with DMSO and methanol and, further, with water to obtain a TEPA-modified non-woven fabric (hereinafter referred to as the non-woven fabric C). The structural formula of the functional group introduced to the non-woven fabric C is shown in Table 1.

Preparation of Sulfoethaneamino-Modified Non-Woven Fabric

To 500 mL of DMSO, 13 g of taurine was added, and triethylamine was further added thereto to a concentration of 473 mM. In the resulting mixture, 10 g of the non-woven fabric B was immersed, and the reaction was allowed to proceed at 70° C. for 6 hours. The non-woven fabric after the reaction was washed with DMSO and methanol and, further, with water to obtain a sulfoethaneamino-modified non-woven fabric (hereinafter referred to as the non-woven fabric D). The structural formula of the functional group introduced to the non-woven fabric D is shown in Table 1.

Preparation of Sulfopropaneamino-Modified Non-Woven Fabric

To 500 mL of DMSO, 13 g of homotaurine was added, and triethylamine was further added thereto to a concentration of 473 mM. In the resulting mixture, 10 g of the non-woven fabric B was immersed, and the reaction was allowed to proceed at 70° C. for 6 hours. The non-woven fabric after the reaction was washed with DMSO and methanol and, further, with water to obtain a sulfopropaneamino-modified non-woven fabric (hereinafter referred to as non-woven fabric E). The structural formula of the functional group introduced to the non-woven fabric E is shown in Table 1.

Preparation of Methylsulfoethaneamino-Modified Non-Woven Fabric

To 500 mL of DMSO, 4.2 g of N-methyltaurine and 5 g of potassium iodide were added, and triethylamine was further added thereto to a concentration of 473 mM. In the resulting mixture, 10 g of the non-woven fabric B was immersed, and the reaction was allowed to proceed at 60° C. for 6 hours. The non-woven fabric after the reaction was washed with DMSO and methanol and, further, with water to obtain a methylsulfoethaneamino-modified non-woven fabric (hereinafter referred to as the non-woven fabric F). The structural formula of the functional group introduced to the non-woven fabric E is shown in Table 1.

Preparation of Dimethylamino-Modified Non-Woven Fabric

To 500 mL of DMSO, 2.5 g of dimethylamine and 5 g of potassium iodide were added, and triethylamine was further added thereto to a concentration of 473 mM. In the resulting mixture, 10 g of the non-woven fabric B was immersed and the reaction was allowed to proceed at 50° C. for 8 hours. The non-woven fabric after the reaction was washed with DMSO and methanol and, further, with water to obtain a dimethylamino-modified non-woven fabric (hereinafter referred to as the non-woven fabric G). The structural formula of the functional group introduced to the non-woven fabric F is shown in Table 1.

Preparation of Dimethylsulfopropaneamino-Modified Non-Woven Fabric

To 465 mL of THF, 9.77 mL of propanesulton was added and the resulting mixture was mixed, followed by immersing 10 g of the non-woven fabric G therein and allowing the reaction to proceed at 50° C. for 6 hours. The non-woven fabric after the reaction was washed with THF and methanol and, further, with water to obtain a dimethylsulfopropaneamino-modified non-woven fabric (hereinafter referred to as the non-woven fabric H). The structural formula of the functional group introduced to the non-woven fabric H is shown in Table 1.

Preparation of Mercaptoethaneamino-Modified Non-Woven Fabric

To 500 mL of DMSO, 11.6 g of aminoethanethiol hydrochloride was added, and triethylamine was further added thereto to a concentration of 473 mM. In the resulting mixture, 10 g of the non-woven fabric B was immersed and the reaction was allowed to proceed at 70° C. for 6 hours. The non-woven fabric after the reaction was washed with DMSO and methanol and, further, with water to obtain a mercaptoethaneamino-modified non-woven fabric (hereinafter referred to as the non-woven fabric I). The structural formula of the functional group introduced to the non-woven fabric I is shown in Table 1.

Preparation of Dimethylmercaptoethaneamino-Modified Non-Woven Fabric

To 500 mL of DMSO, 4.2 g of dimethylaminoethanethiol hydrochloride and 5 g of potassium iodide were added, and triethylamine was further added thereto to a concentration of 473 mM. In the resulting mixture, 10 g of the non-woven fabric B was immersed and the reaction was allowed to proceed at 60° C. for 6 hours. The non-woven fabric after the reaction was washed with DMSO and methanol and, further, with water to obtain a dimethylmercaptoethane-amino-modified non-woven fabric (hereinafter referred to as the non-woven fabric J). The structural formula of the functional group introduced to the non-woven fabric J is shown in Table 1.

Preparation of Chloroacetamidomethyl-Modified Polysulfone

To 32 mL of 5 wt % polysulfone/nitrobenzene solution, 2 mL of 2 wt % NMCA/sulfuric acid solution prepared at 0° C. was added and the resulting mixture was stirred for 1 hour. To this mixture, 800 mL of ice-cold methanol was added to precipitate chloroacetamidomethyl-modified polysulfone, which was then recovered. The recovered chloroacetamidomethyl-modified polysulfone was dissolved in 20 mL of dimethylformamide (hereinafter referred to as DMF), and 400 mL of ice-cold methanol was added again to the resulting solution to obtain chloroacetamidomethyl-modified polysulfone.

Preparation of Tetraethylenepentamine-Modified Polysulfone Non-Woven Fabric

In 30 mL of DMF, 1 g of the chloroacetamidomethyl-modified polysulfone was dissolved and tetraethylenepentamine was added to the resulting solution to a concentration of 20 mM. The resulting mixture was stirred for 17 hours, and 600 mL of ice-cold methanol was added thereto to precipitate tetraethylenepentamine-modified polysulfone, which was then recovered. The recovered tetraethylenepentamine-modified polysulfone was dissolved again in 20 mL of DMF, and 0.1 g of the non-woven fabric A was immersed in the resulting solution. The non-woven fabric A was then immediately removed from the solution and, further, immersed in methanol to obtain a tetraethylenepentamine-modified polysulfone non-woven fabric (hereinafter referred to as the non-woven fabric K). The structural formula of the functional group introduced to the non-woven fabric I is shown in Table 1.

Preparation of Sulfoethaneamino-Modified Polysulfone Non-Woven Fabric

In 30 mL of DMF, 1 g of the chloroacetamidomethyl-modified polysulfone was dissolved and taurine was added to the resulting solution to a concentration of 200 mM. The resulting mixture was stirred for 17 hours and 600 mL of ice-cold methanol was added thereto to precipitate sulfoethaneamino-modified polysulfone, which was then recovered. The recovered sulfoethaneamino-modified polysulfone was dissolved again in 20 mL of DMF, and 0.1 g of the non-woven fabric A was immersed in the resulting solution. The non-woven fabric A was then immediately removed from the solution and, further, immersed in methanol to obtain a sulfoethaneamino-modified polysulfone non-woven fabric (hereinafter referred to as the non-woven fabric L). The structural formula of the functional group introduced to the non-woven fabric L is shown in Table 1.

Preparation of Sulfopropaneamino-Modified Polysulfone Non-Woven Fabric

In 30 mL of DMF, 1 g of the chloroacetamidomethyl-modified polysulfone was dissolved and homotaurine was added to the resulting solution to a concentration of 200 mM. The resulting mixture was stirred for 17 hours and 600 mL of ice-cold methanol was added thereto to precipitate sulfopropaneamino-modified polysulfone, which was then recovered. The recovered sulfopropaneamino-modified polysulfone was dissolved again in 20 mL of DMF, and 0.1 g of the non-woven fabric A was immersed in the resulting solution. The non-woven fabric A was then immediately removed from the solution and, further, immersed in methanol to obtain a sulfopropaneamino-modified polysulfone non-woven fabric (hereinafter referred to as the non-woven fabric M). The structural formula of the functional group introduced to the non-woven fabric M is shown in Table 1.

Preparation of Mercaptoethaneamino-Modified Polysulfone Non-Woven Fabric

In 30 mL of DMF, 1 g of the chloroacetamidomethyl-modified polysulfone was dissolved, and aminoethanethiol hydrochloride was added to the resulting solution to a concentration of 200 mM. The resulting mixture was stirred for 17 hours and 600 mL of ice-cold methanol was added thereto to precipitate mercaptoethaneamino-modified polysulfone, which was then recovered. The recovered mercaptoethaneamino-modified polysulfone was dissolved again in 20 mL of DMF and 0.1 g of the non-woven fabric A was immersed in the resulting solution. The non-woven fabric A was then immediately removed from the solution and, further, immersed in methanol to obtain a mercaptoethaneamino-modified polysulfone non-woven fabric (hereinafter referred to as the non-woven fabric N). The structural formula of the functional group introduced to the non-woven fabric N is shown in Table 1.

TABLE 1

| Non-woven fabric | Introduced functional group (the wavy line represents the surface of the water-insoluble carrier) |
|---|---|
| Non-woven fabric C, K | [structure: ~CH2-NH-C(=O)-CH2-(NH-CH2CH2)4-NH2] |
| Non-woven fabric D, L | [structure: ~CH2-NH-C(=O)-CH2-NH-CH2CH2-S(=O)2-OH] |
| Non-woven fabric E, M | [structure: ~CH2-NH-C(=O)-CH2-NH-CH2CH2CH2-S(=O)2-OH] |
| Non-woven fabric F | [structure: ~CH2-NH-C(=O)-CH2-N(CH3)-CH2-S(=O)2-OH] |
| Non-woven fabric G | [structure: ~CH2-NH-C(=O)-CH2-N(CH3)2] |
| Non-woven fabric H | [structure: ~CH2-NH-C(=O)-CH2-N+(CH3)2-CH2CH2CH2-S(=O)2-OH] |
| Non-woven fabric I, N | [structure: ~CH2-NH-C(=O)-CH2-NH-CH2CH2-SH] |
| Non-woven fabric J | [structure: ~CH2-NH-C(=O)-CH2-N+(CH3)2-CH2CH2-SH] |

Example 1

The non-woven fabric D was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 1. Measurement of the number of each blood component was carried out using Automated Hematology Analyzer XT-1800i (Sysmex Corporation). The adsorption ratio of each blood component was calculated according to Equations 2 to 4 below. The results are shown in Table 2.

Ratio of granulocyte adsorption (%)={(number of granulocytes in blood before circulation)−(number of granulocytes in blood after circulation)}/(number of granulocytes in blood before circulation)×100    Equation 2.

Ratio of monocyte adsorption (%)={(number of monocytes in blood before circulation)−(number of monocytes in blood after circulation)}/(number of monocytes in blood before circulation)×100   Equation 3.

Ratio of lymphocyte adsorption (%)={(number of lymphocytes in blood before circulation)−(number of lymphocytes in blood after circulation)}/(number of lymphocytes in blood before circulation)×100   Equation 4.

Example 2

The non-woven fabric E was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Example 3

The non-woven fabric F was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Example 4

The non-woven fabric H was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Example 5

The non-woven fabric L was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Example 6

The non-woven fabric M was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Comparative Example 1

The non-woven fabric C was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Comparative Example 2

The non-woven fabric G was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Comparative Example 3

The non-woven fabric I was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Comparative Example 4

The non-woven fabric J was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Comparative Example 5

The non-woven fabric K was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

Comparative Example 6

The non-woven fabric N was cut out into a disk having a diameter of 8 mm, and placed in a polypropylene container. To this container, 1 mL of human blood (heparin concentration, 30 U/mL) was added and the content of the tube was mixed by inversion in an incubator at 37° C. for 20 minutes. Thereafter, the adsorption ratio of each blood component was calculated. The results are shown in Table 2. Measurement of the number of each blood component was carried out using Automated Hematology Analyzer XT-1800i (Sysmex Corporation). The adsorption ratio of each blood component was calculated according to Equations 2 to 4 described above. The results are shown in Table 2.

TABLE 2

| Sample (non-woven fabric) | | Ratio of granulocyte adsorption (%) | Ratio of lymphocyte adsorption (%) | Ratio of monocyte adsorption (%) |
|---|---|---|---|---|
| Example 1 | Non-woven fabric D | 75.4 | 43.8 | 75 |
| Example 2 | Non-woven fabric E | 80.3 | 45.5 | 78 |
| Example 3 | Non-woven fabric F | 94.1 | 36.2 | 95 |
| Example 4 | Non-woven fabric H | 40.5 | 11.4 | 60 |
| Example 5 | Non-woven fabric L | 70.5 | 40.3 | 72 |
| Example 6 | Non-woven fabric M | 77.4 | 41.2 | 75 |
| Comparative Example 1 | Non-woven fabric C | 80.0 | 3.5 | 85 |
| Comparative Example 2 | Non-woven fabric G | 76.3 | 6.6 | 90 |
| Comparative Example 3 | Non-woven fabric I | 35.2 | 0.0 | 26 |
| Comparative Example 4 | Non-woven fabric J | 77.7 | 6.0 | 91 |
| Comparative Example 5 | Non-woven fabric K | 75.2 | 2.5 | 85 |
| Comparative Example 6 | Non-woven fabric N | 44.1 | 0.0 | 40 |

Based on the results in Table 2, it was found that our carriers for blood component adsorption wherein a functional group having an acidic functional group is introduced to the surface of the water-insoluble carrier show remarkably higher adsorption ratios of lymphocytes while maintaining the adsorption ratios of granulocytes and monocytes, compared to the carriers wherein the functional group on the surface of the water-insoluble carrier does not have an acidic functional group.

Example 7

The non-woven fabric D was cut out into two disks each having a diameter of 8 mm, and placed in a polypropylene container. To this container, 0.8 mL of fetal bovine serum (hereinafter referred to as FBS) prepared such that each of IL-8, IL-17 and IFN-γ is contained at a concentration of 500 pg/mL was added, and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the Equations 5 to 7 below. The results are shown in Table 3.

Ratio of IL-8 adsorption (%)={(concentration of IL-8 before mixing by inversion)−(concentration of IL-8 after mixing by inversion)}/(concentration of IL-8 before mixing by inversion)× 100     Equation 5.

Ratio of IL-17 adsorption (%)={(concentration of IL-17 before mixing by inversion)−(concentration of IL-17 after mixing by inversion)}/(concentration of IL-17 before mixing by inversion)×100     Equation 6.

Ratio of IFN-γ adsorption (%)={(concentration of IFN-γ before mixing by inversion)−(concentration of IFN-γ after mixing by inversion)}/(concentration of IFN-γ before mixing by inversion)×100     Equation 7.

Example 8

The non-woven fabric E was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

Example 6

The non-woven fabric F was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

Example 7

The non-woven fabric H was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

Example 8

The non-woven fabric L was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

Example 9

The non-woven fabric M was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

Comparative Example 7

The non-woven fabric C was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

Comparative Example 8

The non-woven fabric G was cut out into two disks each having a diameter of 8 mm, and placed in a polypropylene container. To this container, 0.8 mL of FBS prepared such that each of IL-8 is contained at a concentration of 500 pg/mL was added and the content of the tube was mixed by inversion in an incubator at 37° C. for 1 hour. Thereafter, the remaining concentration of IL-8 was measured by ELISA and the adsorption ratio of IL-8 was calculated according to the above Equation 5. The results are shown in Table 3.

Comparative Example 9

The non-woven fabric I was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

Comparative Example 10

The non-woven fabric J was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

Comparative Example 11

The non-woven fabric K was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

Comparative Example 12

The non-woven fabric N was cut out into two disks each having a diameter of 8 mm, and placed in a polypropylene container. To this container, 0.8 mL of FBS prepared such that each of IL-8, IL-17 and IFN-γ is contained at a concentration of 500 pg/mL was added and the content of the tube was mixed by inversion in an incubator at 37° C. for 1 hour. Thereafter, the remaining concentration of each of IL-8, IL-17 and IFN-γ was measured by ELISA and the adsorption ratios of IL-8, IL-17 and IFN-γ were calculated according to the above Equations 5 to 7. The results are shown in Table 3.

TABLE 3

| Sample (non-woven fabric) | | Ratio of IL-8 adsorption (%) | Ratio of IL-17 adsorption (%) | Ratio of IFN-γ adsorption (%) |
| --- | --- | --- | --- | --- |
| Example 7 | Non-woven fabric D | 97.7 | 92.5 | 44.4 |
| Example 8 | Non-woven fabric E | 98.0 | 90.2 | 35.3 |
| Example 9 | Non-woven fabric F | 96.9 | 95.8 | 82.1 |
| Example 10 | Non-woven fabric H | 83.2 | 80.5 | 65.3 |
| Example 11 | Non-woven fabric L | 95.2 | 90.3 | 54.5 |
| Example 12 | Non-woven fabric M | 97.5 | 90.0 | 38.4 |
| Comparative Example 7 | Non-woven fabric C | 97.5 | 88.8 | 79.2 |

TABLE 3-continued

| Sample (non-woven fabric) | | Ratio of IL-8 adsorption (%) | Ratio of IL-17 adsorption (%) | Ratio of IFN-γ adsorption (%) |
|---|---|---|---|---|
| Comparative Example 8 | Non-woven fabric G | 0.0 | — | — |
| Comparative Example 9 | Non-woven fabric I | 4.4 | 0.0 | 14.0 |
| Comparative Example 10 | Non-woven fabric J | 0.0 | 0.0 | 0.0 |
| Comparative Example 11 | Non-woven fabric K | 98.2 | 75.4 | 80.1 |
| Comparative Example 12 | Non-woven fabric N | 2.1 | 0.0 | 7.5 |

Based on the results in Table 3, it was found that our carriers for blood component adsorption wherein a functional group having an acidic functional group is introduced to the surface of the water-insoluble carrier show higher adsorption ratios of IL-8, IL-17 and IFN-γ compared to the carriers wherein the functional group on the surface of the water-insoluble carrier does not have an acidic functional group.

INDUSTRIAL APPLICABILITY

Our carriers can be used as a column for adsorption of blood components in the field of medical care.

The invention claimed is:

1. A water-insoluble carrier comprising a fiber, said water-insoluble carrier having a surface to which functional groups are immobilized, said functional groups containing an acidic functional group selected from the group consisting of a sulfite group and sulfonate group; and containing a tertiary amino group,
    said fiber having a fiber diameter of 0.5 to 20 um,
    said water-insoluble carrier having a negative charge of $1.5 \times 10^{-5}$ to $1.5 \times 10^{-3}$ eq/g,
    a material of said water-insoluble carrier composed of a fiber is at least one selected from the group consisting of polystyrenes, polypropylene, polypropylene-polyethylene copolymers, or poly(p-phenylene ether sulfone), and
    said acidic functional group is positioned at a terminus of said functional group and said acidic functional group is positioned at a side not bound to said water-insoluble carrier.

2. The water-insoluble carrier according to claim 1, wherein said water-insoluble carrier has a porosity of 85 to 98%, wherein said "porosity" is a ratio of a volume of voids in the water-insoluble carrier, and means a percentage value calculated by dividing the volume of voids in the water-insoluble carrier by an apparent volume of the water-insoluble carrier and said porosity is calculated by Equation (1):

$$\text{Porosity (\%)} = \{(b-a)/b\} \times 100 \quad (1)$$

a: The area of the part occupied by the water-insoluble carrier
b: The total area of the cross-section of the carrier for blood component adsorption.

3. The water-insoluble carrier according to claim 1, wherein said water-insoluble carrier comprises fibers having a fiber diameter of 4 to 10 μm.

4. The water-insoluble carrier according to claim 1, wherein said acidic functional group and said amino group are linked together via an alkyl chain.

5. The water-insoluble carrier according to claim 4, wherein said alkyl chain is an alkyl chain having not more than 3 carbon atoms.

6. A column for blood component adsorption filled with a water-insoluble carrier comprising a fiber or particle, said water-insoluble carrier having a surface to which functional groups are immobilized, said functional groups containing an acidic functional group selected from the group consisting of a sulfite group and sulfonate group; and containing a tertiary amino group,
    said fiber having a fiber diameter of 0.5 to 20 um, and
    said water-insoluble carrier having a negative charge of $1.5 \times 10^{-5}$ to $1.5 \times 10^{-3}$ eq/g,
    a material of said water-insoluble carrier composed of a fiber is at least one selected from the group consisting of polystyrenes, polypropylene, polypropylene-polyethylene copolymers, or poly(p-phenylene ether sulfone), and
    said acidic functional group is positioned at a terminus of said functional group and said acidic functional group is positioned at a side not bound to said water-insoluble carrier.

7. The water-insoluble carrier according to claim 2, wherein said water-insoluble carrier comprises fibers having a fiber diameter of 4 to 10 μm.

8. The water-insoluble carrier according to claim 2, wherein said acidic functional group and said amino group are linked together via an alkyl chain.

9. The water-insoluble carrier according to claim 3, wherein said acidic functional group and said amino group are linked together via an alkyl chain.

10. The column for blood component adsorption according to claim 6, wherein said water-insoluble carrier has a porosity of 85 to 98%, wherein said "porosity" is a ratio of a volume of voids in the water-insoluble carrier, and means a percentage value calculated by dividing the volume of voids in the water-insoluble carrier by an apparent volume of the water-insoluble carrier and said porosity is calculated by Equation (1):

$$\text{Porosity (\%)} = \{(b-a)/b\} \times 100 \quad (1)$$

a: The area of the part occupied by the water-insoluble carrier
b: The total area of the cross-section of the carrier for blood component adsorption.

11. The column for blood component adsorption according to claim 6, wherein said water-insoluble carrier has a porosity of 85 to 98%, and said water-insoluble carrier comprises fibers having a fiber diameter of 4 to 10 μm.

12. The column for blood component adsorption according to claim 6, wherein said acidic functional group and said amino group are linked together via an alkyl chain.

13. The column for blood component adsorption according to claim 12, wherein said alkyl chain is an alkyl chain having not more than 3 carbon atoms.

* * * * *

UNITED STATES PATENT AND TRADEMARK OFFICE
CERTIFICATE OF CORRECTION

PATENT NO. : 9,802,178 B2
APPLICATION NO. : 13/881172
DATED : October 31, 2017
INVENTOR(S) : Tomita et al.

Page 1 of 1

It is certified that error appears in the above-identified patent and that said Letters Patent is hereby corrected as shown below:

In the Claims

At Column 17, at Line 36, please change "20 um" to --20 μm--.

At Column 18, at Line 11, please delete "or particle"; and at Line 17, please change "20 um" to --20 μm--.

Signed and Sealed this
Twelfth Day of June, 2018

Andrei Iancu
*Director of the United States Patent and Trademark Office*